(12) United States Patent
Kalkman et al.

(10) Patent No.: US 8,322,190 B2
(45) Date of Patent: Dec. 4, 2012

(54) OPTICAL CAVITY-ENHANCED PHOTO ACOUSTIC TRACE GAS DETECTOR WITH VARIABLE LIGHT INTENSITY MODULATOR

(75) Inventors: Jeroen Kalkman, Eindhoven (NL); Maarten Marinus Johannes Wilhelm Van Herpen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 420 days.

(21) Appl. No.: 12/438,573

(22) PCT Filed: Aug. 27, 2007

(86) PCT No.: PCT/IB2007/053408
§ 371 (c)(1),
(2), (4) Date: Feb. 24, 2009

(87) PCT Pub. No.: WO2008/026146
PCT Pub. Date: Mar. 6, 2008

(65) Prior Publication Data
US 2009/0288474 A1 Nov. 26, 2009

(30) Foreign Application Priority Data
Aug. 31, 2006 (EP) .................................... 06119854

(51) Int. Cl.
*G01N 21/17* (2006.01)
(52) U.S. Cl. ...................................... 73/24.02; 73/24.06
(58) Field of Classification Search ................. 73/24.02, 73/24.06
See application file for complete search history.

(56) References Cited

U.S. PATENT DOCUMENTS

| | | | | |
|---|---|---|---|---|
| 3,730,629 A | * | 5/1973 | Rentzepis | 356/300 |
| 3,793,771 A | * | 2/1974 | Slaughter | 47/44 |
| 3,893,771 A | * | 7/1975 | Bell | 356/402 |
| 4,105,919 A | | 8/1978 | Bridges et al. | |
| 4,908,510 A | | 3/1990 | Huggins et al. | |

(Continued)

FOREIGN PATENT DOCUMENTS
EP 0598949 A1 6/1994
(Continued)

OTHER PUBLICATIONS

Davidsson, J. et al., "Experimental Improvements in Recording Gas-Phase Photoacoustic Spectra", The Journal of Physical Chemistry, vol. 94, No. 10, 1990, pp. 4069-4073.*

(Continued)

*Primary Examiner* — Daniel Larkin

(57) ABSTRACT

A photo acoustic trace gas detector for detecting a concentration of a trace gas in a gas mixture. The detector includes a light source for producing a light beam and a light modulator for modulating the light beam into a series of light pulses for generating sound waves in the gas mixture. The light modulator is arranged for modulating the light beam between a non-zero lower intensity level and a higher intensity level. An amplitude of the sound waves being a measure of the concentration. An optical cavity contains the gas mixture and amplifies a light intensity of the light pulses. A transducer converts the sound waves into electrical signals. A feedback loop with a photo detector for measuring the light intensity of the light pulses regulates the amplification of the light intensity in the optical cavity.

8 Claims, 8 Drawing Sheets

U.S. PATENT DOCUMENTS

| | | | |
|---|---|---|---|
| 5,348,002 | A | 9/1994 | Caro |
| 7,101,340 | B1 * | 9/2006 | Braun .......................... 600/532 |
| 2004/0095579 | A1 | 5/2004 | Bisson et al. |
| 2005/0117155 | A1 | 6/2005 | Kosterev |
| 2005/0206903 | A1 * | 9/2005 | Tan et al. ...................... 356/437 |
| 2006/0123884 | A1 | 6/2006 | Selker et al. |

FOREIGN PATENT DOCUMENTS

| | | |
|---|---|---|
| GB | 749689 A | 5/1956 |
| JP | 54141194 A | 11/1979 |

OTHER PUBLICATIONS

Fink, T. et al., "An Improved CO2 Laser Intracavity Photoacoustic Spectrometer for Trace Gas Analysis", Rev. Sci. Instrum., vol. 67, No. 11, Nov. 1996, pp. 4000-4004.*

Rossi Alessandro et al: "Optical enhancement of diode laser-photoacoustic trace gas detection by means of external Fabry-Perot cavity" Applied Physics Letters, AIP, America Institute of Physics, Melville, NY, US, vol. 87, No. 4, Jul. 22, 2005, pp. 41110-1-41110-3, XP012077218 ISSN: 0003-6951.

* cited by examiner

US 8,322,190 B2

OPTICAL CAVITY-ENHANCED PHOTO ACOUSTIC TRACE GAS DETECTOR WITH VARIABLE LIGHT INTENSITY MODULATOR

TECHNICAL FIELD OF THE INVENTION

The invention relates to a photo acoustic trace gas detector for detecting a concentration of a trace gas in a gas mixture, the photo acoustic trace gas detector comprising a light source for producing a light beam, a light modulator for modulating the light beam into a series of light pulses for generating sound waves in the gas mixture, an amplitude of the sound waves being a measure of the concentration, an optical cavity for containing the gas mixture and for amplification of a light intensity of the light pulses, a transducer for converting the sound waves into electrical signals, and a feedback loop for regulating the amplification of the light intensity of the light pulses in the optical cavity, the feedback loop comprising a photo detector for measuring the light intensity of the light pulses.

BACKGROUND OF THE INVENTION

Such a detector is known from the article "Optical enhancement of diode laser-photo acoustic trace gas detection by means of external Fabry-Perot cavity" by Rossi et al., published in Applied Physics Letters, vol. 87, 2005. The detector described therein sends a chopped laser beam through a gas contained in an acoustic cell. The laser beam is chopped by a rotating disc chopper that periodically interrupts the light beam. The laser wavelength is tuned to excite particular molecules of the gas into a higher energy level. This excitation leads to an increase of the thermal energy, resulting in a local rise of the temperature and the pressure inside the acoustic cell. If the chopping frequency matches a resonance frequency of the acoustic cell, the pressure variations result in a standing acoustic wave. The acoustic waves are detected by a microphone in the acoustic cell. The resonance frequency of such an acoustic cell is typically of the order of a few kHz. In the detector of Rossi et al., a chopping frequency of 2.6 kHz is used.

Rossi et al. also describe using a Fabry-Perot cavity for amplifying the light intensity in the acoustic cell by locking the laser wavelength to the cavity length. The amplification is very advantageous because the sensitivity of the detector is proportional to the laser power. A feedback signal is obtained from a photodiode placed behind the Fabry-Perot cavity. The intensity transmitted through the cavity is used for feedback on the laser wavelength. It has the drawback that no feedback signal is present when the chopper blocks the laser beam and the transmitted intensity is zero. Therefore, no cavity feedback can be given to the laser during these periods and the cavity can become unlocked when it is disturbed. The result is a loss of optical power and a concomitant decrease of photo acoustic signal strength. The solution presented by Rossi et al. uses signal demodulation with a large time constant such that the generated feedback signal is the average over a number of periods. Consequently, the cavity locking mechanism is slow.

An important application of photo acoustic trace gas detectors is breath testing. Breath testing is a promising area of medical technology. Breath tests are non-invasive, user friendly and low cost. Prime examples of breath testing are monitoring of asthma, alcohol breath testing and detection of stomach disorders and acute organ rejection. First clinical trials show possible applications in the pre-screening of breast and lung cancer. These volatile biomarkers have typical concentrations in the parts per billion (ppb) range. Nitric oxide (NO) is one of the most important trace gases in the human breath, and elevated concentrations of NO can be found in asthmatic patients. Currently, exhaled NO levels at ppb concentrations can be only measured using expensive and bulky equipment based on chemiluminescence or optical absorption spectroscopy. A compact, hand-held, and low-cost NO sensor forms an interesting device that can be used to diagnose and monitor airway inflammation and can be used at the doctor's office and for medication control at home.

It is the challenge for these hand-held gas-analyzing devices to combine sufficient high sensitivity (ppb level) with a high robustness. Current photo acoustic trace gas detectors have the disadvantage that small form factor lasers (i.e. diode lasers) do not have sufficient laser power to reach the sensitivity required for trace gas detection. The use of an optical power enhancement cavity as described by Rossi et al. could increase the optical power, but that would lead to a slow feedback. As described above, when an optical enhancement cavity is used in combination with photo acoustics, the feedback signal is turned on and off intermittently by the chopper. Consequently, the cavity locking mechanism becomes very slow, which results in a system that is not robust enough for portable applications.

SUMMARY OF THE INVENTION

It is an object of the invention to provide a photo acoustic trace gas detector according to the opening paragraph with a fast feedback loop.

According to a first aspect of the invention, this object is achieved by providing a photo acoustic trace gas detector according to the opening paragraph, wherein the light modulator is arranged for modulating the light beam between a non-zero lower intensity level and a higher intensity level.

Because the light intensity does not drop to zero, an uninterrupted feedback signal is provided. In this way a fast and more stable feedback lock loop can be implemented and portable application of the detector is made possible.

In a preferred embodiment, the detector further comprises means for adjusting a height (e.g., amplitude) of the lower intensity level.

The means for adjusting allows the user, or an automated system, to adjust the strength of the feedback signal for the feedback loop with respect to the photo-acoustic modulated signal. When a strong feedback signal is required, more light intensity is used for the feedback loop. In more stable conditions more light intensity may be used for providing the pressure variations in the gas flow cell and less for the feedback signal, resulting in an improved accuracy of the trace gas detector. The means for adjusting may, for example, comprise filters with adjustable transparency.

In a preferred embodiment, the light modulator is arranged for modulating light with a first polarization while not modulating light with a second polarization, and the feedback loop comprises means for only providing the light with the second polarization to the photo detector.

In this embodiment, the light with the second polarization is continuously available for use as a feedback signal, while the light with the first polarization is modulated for causing the desired pressure variations in the gas flow cell. It is an advantage of this embodiment that the feedback signal is relatively stable and is not influenced by the light intensity transitions needed for providing the light pulses.

Preferably, the photo acoustic trace gas detector further comprises a polarization rotator, placed between the light source and the light modulator, for enabling varying a ratio of an intensity of the light with the first polarization and an intensity of the light with the second polarization.

By rotating the polarization of the laser light, the ratio of the intensities of the light with the first and the second polarization can be varied. This allows the user, or an automated system, to adjust the strength of the feedback signal for the feedback loop with respect to the photo-acoustic modulated signal.

In a preferred embodiment the transducer is a crystal oscillator. A crystal oscillator is much more sensitive than the microphone used in the above mentioned prior art system. Consequently, a more sensitive photo acoustic trace gas detector is obtained. As an additional advantage, the high sensitivity of the crystal oscillator makes the use of an acoustic cell not essential and thereby simplifies the construction of the detector.

In a further embodiment the crystal oscillator is a quartz tuning fork. Quartz tuning forks have a high accuracy. Furthermore, quartz tuning forks are not very expensive because they are used on a large scale, for example, for the manufacturing of digital watches.

These and other aspects of the invention are apparent from and will be elucidated with reference to the embodiments described hereinafter.

DETAILED DESCRIPTION OF THE INVENTION

Figure 1A:
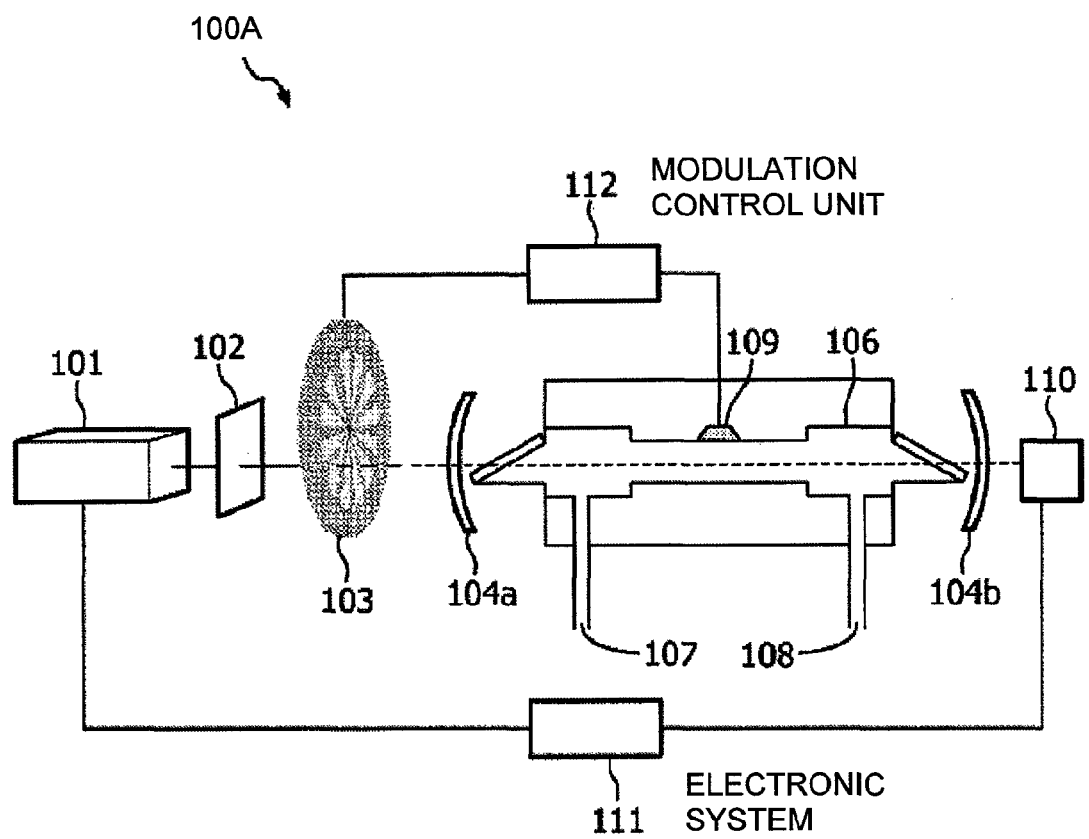
FIG. 1a schematically shows an embodiment of the photo acoustic trace gas detector according to the inventions.

FIG. 1a shows a typical photo acoustic trace gas detector 100A according to the invention. A light source 101 provides a continuous wave laser beam and is modulated into a series of light pulses at a certain 'chopping' frequency by, e.g., a chopper 103, shutter or acousto-optic modulator and a modulation control unit 112. Alternatively, the light source 101 itself may provide the light pulses at a fixed frequency. The light pulses are sent into an optical cavity, which is defined by two semi-transparent mirrors 104a and 104b. An optical isolator 102 is optionally placed between the light source 101 and the input mirror 104a to reduce the reflectance of light from the cavity mirror 104a into the light source 101. The light pulses enter the optical cavity through input mirror 104a and are reflected many times between the two cavity mirrors 104a and 104b. If the distance between the two mirrors 104a and 104b is in resonance with the wavelength of the laser, standing waves occur and the light intensity is amplified. The light that is transmitted by the output mirror 104b is measured with a photo detector 110. The signal from the photo detector 110 is used as a feedback signal for the laser wavelength or the length of the optical cavity.

In a locked cavity scheme the laser and cavity operate at the same fixed wavelength. In most designs either the laser wavelength or cavity length is modulated and the transmission or reflection of the laser through the cavity is monitored with a photo detector 110. The change in transmission is then used as a feedback signal that is used to either drive an actuator, e.g. a piezo driver, attached to one of the cavity mirrors 104a, 104b (cavity length modulation) or to set the laser frequency (laser wavelength modulation). The wavelength of the laser is typically scanned on the flank of a cavity resonance if it is locked to the cavity. When the laser wavelength gets out of resonance with the cavity (not including the small wavelength modulation of the laser) the transmitted intensity changes. A feedback signal is then sent to the laser diode 101 to correct the wavelength and bring the transmission back towards the desired level. Note that at maximum cavity transmission the wavelength modulation of the laser does typically not result in a change in transmission. Therefore the cavity should preferably be operated just below maximum transmission. When the laser intensity changes (due to laser instability) the height of the resonance peak changes with a consequent change of the feedback amplitude as a result. The locking mechanism will move the laser to another frequency on the new resonance curve until a new equilibrium is achieved.

Inside the optical cavity a gas cell 106 is situated for containing the gas sample to be examined. Alternatively, the optical cavity is enclosed by the gas cell 106. Optionally, the gas cell 106 comprises a gas inlet 107 and a gas outlet 108 for allowing a gas flow through the gas cell 106. If the laser wavelength is tuned to a molecular transition, i.e. $E_I \rightarrow E_K$, some of the gas molecules in the lower level $E_I$ will be excited into the upper level $E_K$. By collisions with other atoms or molecules these excited molecules may transfer their excitation energy into translational, rotational, or vibrational energy of the collision partners. At thermal equilibrium this causes an increase of the thermal energy, resulting in a local rise of the temperature and pressure inside the gas cell 106. Every pulse of light will cause an increase in pressure after which the pressure can reduce again, before the next pulse arrives. This increase and decrease of pressure will result in an acoustic wave at the chopping frequency. Centered in the middle of the gas cell 106 is a transducer 109, e.g. a microphone that can pick up the acoustic wave generated by the absorbed light in the gas. Preferably, the transducer 109 is a crystal oscillator, e.g. a quartz tuning fork, with a resonance frequency that can pick up the acoustic wave generated by the absorbed light in the gas. The use of a crystal oscillator may make the acoustic cell unnecessary.

Figure 2A:
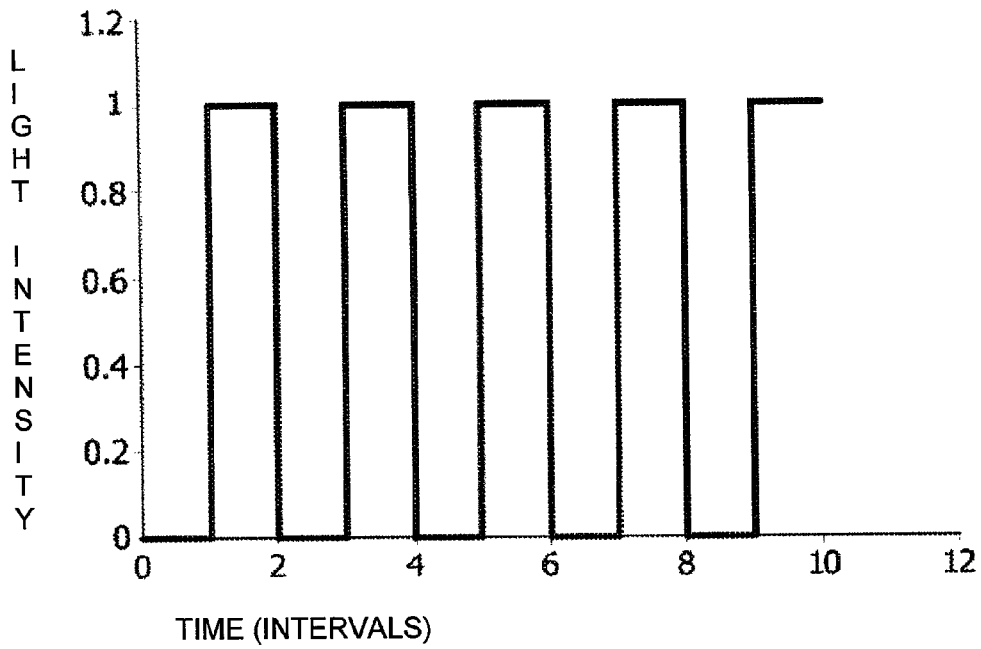
FIG. 2a shows a time dependence of the light intensity of the modulated light according to the prior art.

FIG. 2a shows the light intensity (y-axis) of the modulated light as a function of the progress of time (x-axis) in a prior art detector. In, for example, the trace gas detector according to Rossi et al. the light beam is blocked periodically in order to create light pulses from the continuous wave laser beam from the laser source. As a result, the light intensity of the modulated light is zero during the periods between two pulses and the feedback signal is interrupted. The interruption period can not be easily shortened, because a detector using a higher chopping frequency would require an acoustic cell with so small dimensions that it becomes inefficient.

Figure 2B:
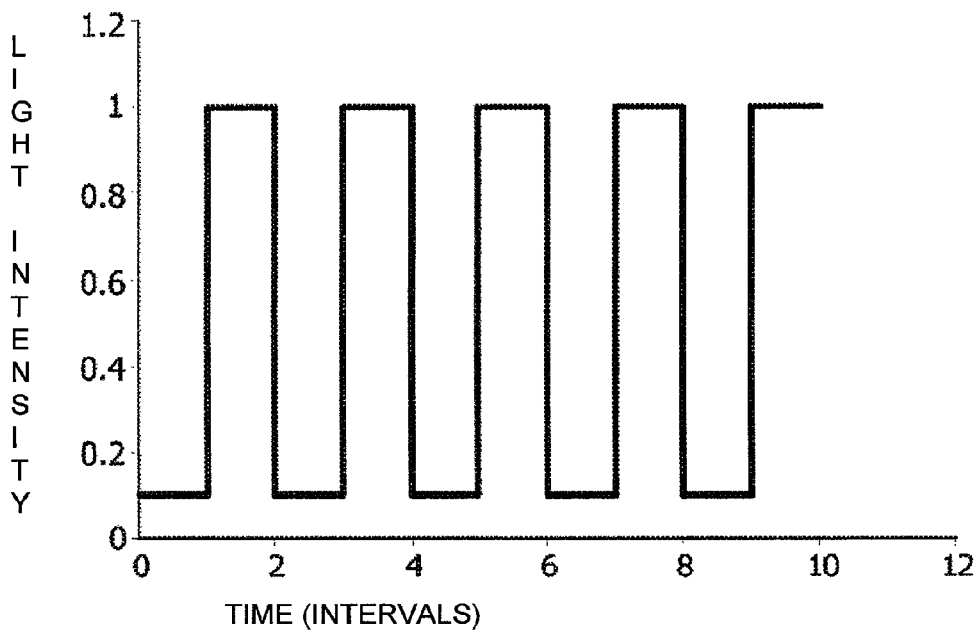
FIG. 2b shows a time dependence of the light intensity of the modulated light according to an embodiment of the invention.

FIG. 2b shows a time dependence of the light intensity of the modulated light according to an embodiment of the invention. Here, the light is modulated in such a way that the light intensity never drops to zero. The light is modulated between a higher and a lower intensity level, the lower level being substantially higher than zero. In this way, the feedback signal is never interrupted and the response time of the feedback loop may be much shorter than in the prior art situation.

Figure 3:
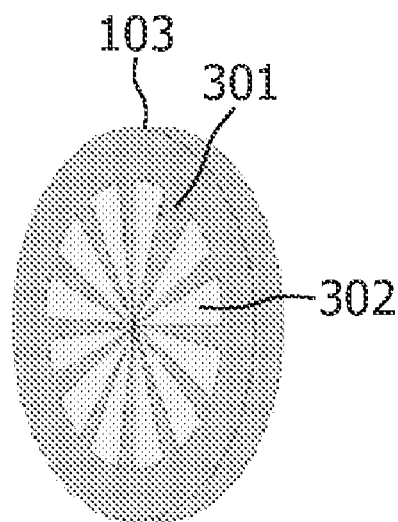
FIG. 3 shows two choppers that are arranged for use with the trace gas detector according to the invention.
Figure 3:
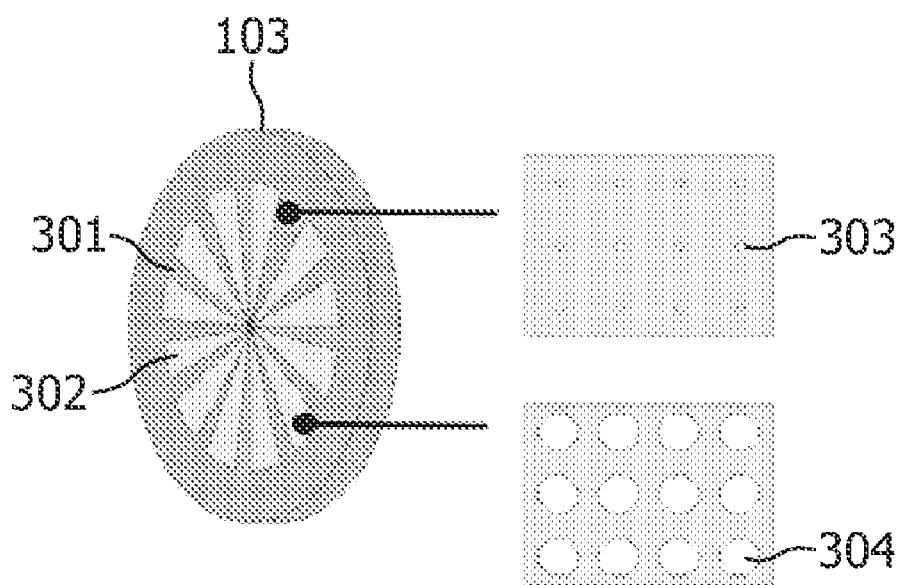

FIG. 3 shows two choppers 103 which are arranged for use with the trace gas detector 100 according to the invention. The choppers 103 are used for modulating the light beam into a series of light pulses. The choppers 103 in FIG. 3 are rotatable discs with first segments 301 with a lower transmission coefficient and second segments 302 with a higher transmission coefficient. The lower transmission coefficient is substantially higher than zero. The higher transmission coefficient is higher than the first transmission coefficient and preferably equal to or approximately one. In operation, the chopper 103 is rotated at a constant angular velocity. When the light beam shines on a segment 301 with a lower transmission coefficient, most of the light is blocked. Behind the chopper 103, a low intensity light beam does not excite many molecules in the gas, but provides sufficient light for the photo detector 110 to provide a feedback signal. When the light beam shines on a segment 302 with a higher transmission coefficient, all or most of the light is transmitted. Behind the chopper 103, a high intensity light beam excites many molecules in the gas (if available) which causes an increase of the thermal energy, resulting in a local rise of the temperature and pressure inside the gas cell 106. The transmission coefficients of the segments may be realized by using absorption filters or a reflection filter. The second embodiment shown in FIG. 3 uses plates with an array of small holes 303 and large holes 304 to modulate the intensity between the low level and the high level, correspondingly. Slits may be used instead of holes. Alternatively, the density of the holes or slits can be varied instead of their size. The total area of the holes or slits is proportional to the required transmission. To achieve a relatively constant intensity in either modulation state, the holes or slits should be much smaller than the beam diameter. If necessary this can be achieved with a beam expander followed by a collimator. The frequency of the light pulses and the resulting acoustic waves depends on the angular velocity of the chopper 103 and the number of segments on the disc. The strength of the acousto-optic signal is proportional to the difference between the high intensity level of the pulses and the low intensity level during the darker periods. Instead of the choppers 103, other kinds of modulators like, e.g., a shutter or acousto-optic modulator may be used.

Figure 4:
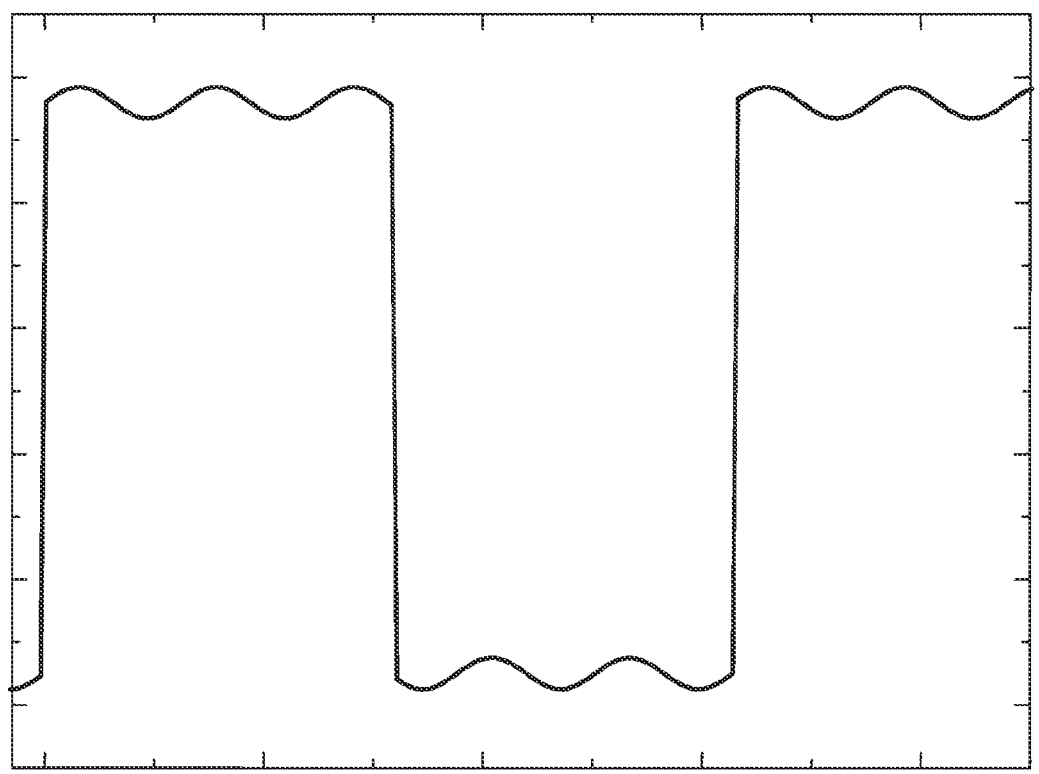
FIG. 4 shows a time dependence of the light intensity of the modulated light according to a further embodiment of the invention.

FIG. 4 shows a time dependence of the light intensity of the modulated light according to a further embodiment of the invention. The light intensity has a low frequency chopping component for photo-acoustic detection and a high frequency modulation for cavity locking. The high frequency modulation may be provided by modulating the laser wavelength around an average wavelength. Alternatively the cavity length can be modulated using, e.g., piezo drivers attached to one of the cavity mirrors 104a, 104b. The wavelength of the laser is typically scanned on the flank of a cavity resonance if it is locked to the cavity. When the laser wavelength gets out of resonance with the cavity (not including the small wavelength modulation of the laser) the transmitted intensity changes. A feedback signal is then sent to the laser diode 101 to correct the wavelength and bring the transmission back towards the desired level. Note that at maximum cavity transmission the wavelength modulation of the laser does not result in a change in transmission. Therefore the cavity should be operated just below maximum transmission. When the laser intensity changes (due to laser instability) the height of the resonance peak changes with a consequent change of the feedback amplitude as a result.

Figure 5:
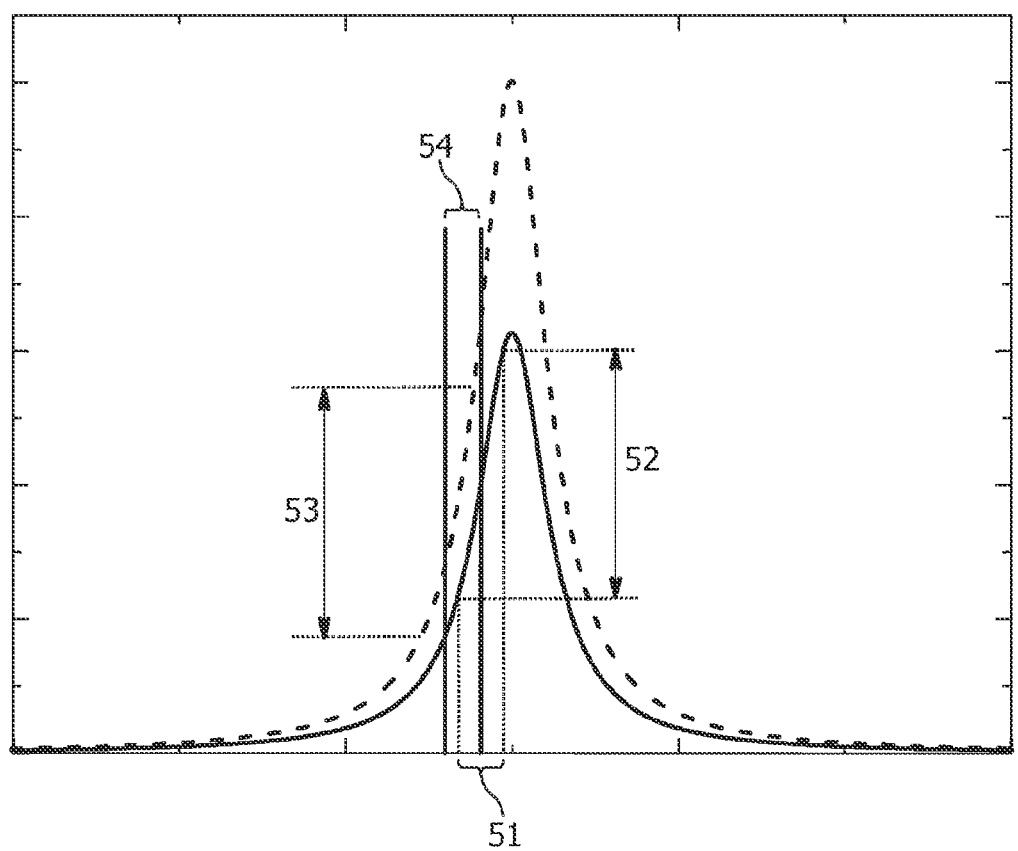
FIG. 5 shows a wavelength dependence of the modulated light according to an embodiment of the invention.

FIG. 5 shows a wavelength dependence of the modulated light according to an embodiment of the invention. The modulation of the light intensity at the chopping frequency results in a small wavelength shift as shown in FIG. 5. The high frequency wavelength modulation over a small wavelength interval 51 results in an intensity modulation along the slope of the cavity resonance with a certain amplitude 52. When the transmission changes from low to high, the height of the resonance peak increases in amplitude. Consequently, the slope of the resonance curve and the feedback amplitude are changed. Since the feedback amplitude 53 has to remain constant a feedback signal is sent to the laser to change the center wavelength of the laser to achieve the same feedback amplitude. This will result in a small wavelength shift 54. This unwanted wavelength shift 54 does not occur with the embodiment described below with reference to FIG. 6.

Figure 1B:
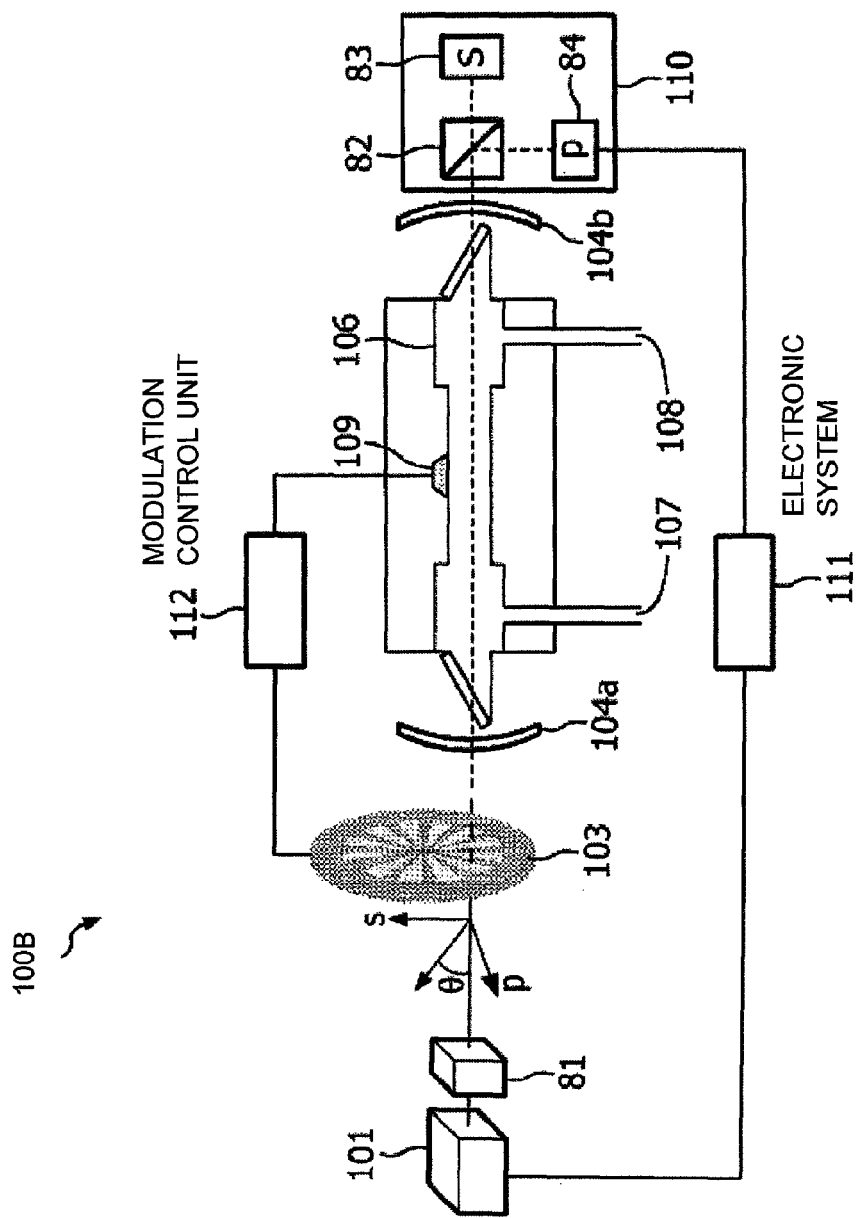
FIG. 1b schematically shows a further embodiment of the photo acoustic trace gas detector according to the invention.

FIG. 1b shows a preferred embodiment of a photo acoustic trace gas detector 100B according to the invention. This embodiment uses a polarization dependant modulator 103, which results in the modulation of the polarized beam used for photo-acoustic excitation of trace gas molecules, but does not modulate the orthogonally polarized beam used for feedback. This may be accomplished by placing an alternating series of 'p' polarizers and open blades along the perimeter of a mechanical chopper. The 's' beam is blocked by the 'p' polarizer, while the 'p' beam is not affected by any of the blades of the chopper and therefore has a constant amplitude. The laser is mounted under an angle such that the output beam contains both a 'p' and an 's' component. The beam then enters the whole gas analysis system, as shown in FIG. 1a, and is split by a polarizing beam splitter 82 downstream of the optical cavity. The transmitted 's' polarized beam may then be measured by a first photo detector 83 to serve as a reference signal to the photo-acoustic signal. The transmitted 'p' polarized beam is detected by second photo detector 84 and is demodulated using electronic system 111 where its amplitude is used to lock the laser to the cavity. The purpose of the modulator 103 is to modulate the 's' beam for photo-acoustic excitation of the trace gas, while simultaneously achieving a constant transmission for the 'p' beam for cavity locking. Because of this constant transmission, this embodiment does not show the wavelength shift 54 of the embodiment described and shown in FIG. 5 and is therefore not very stable.

In a preferred embodiment, the detector comprises a polarization rotator 81, placed between the light source 101 and the light modulator 103, for enabling varying a ratio of the intensity of the light with the different polarizations. In stable conditions, when the feedback is not very important, the intensity of the light used for the feedback loop is decreased and the intensity of the light used for the photo acoustic detection is increased.

Figure 6A:
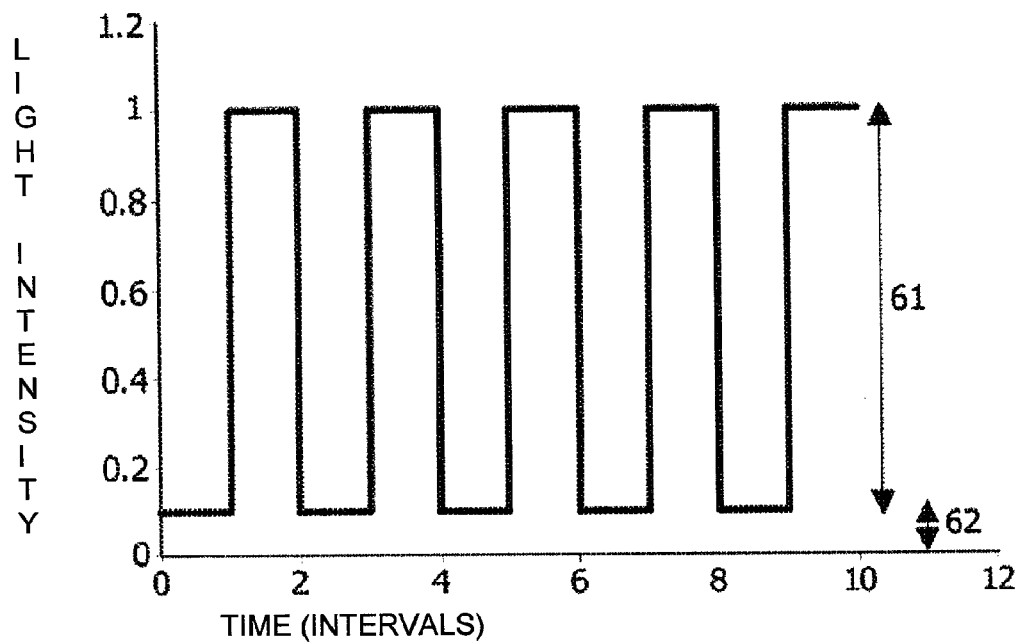
FIGS. 6a and 6b show two time dependences of the light intensity of the modulated light according to embodiments of the invention comprising a polarization dependent modulator.
Figure 6B:
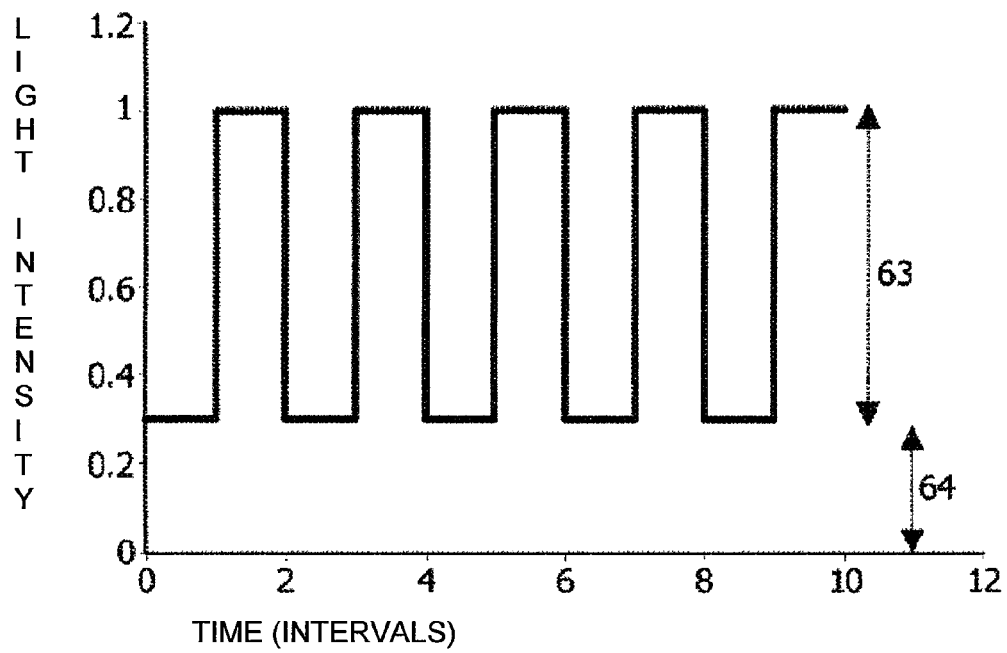

FIGS. 6a and 6b show two time dependences of the light intensity of the modulated light according to an embodiment of the invention comprising a polarization rotator 81 and a polarization dependent modulator 103. In the situation shown in FIG. 6a, the 's' polarized component is relatively large. FIG. 6a shows the total light intensity (the sum of 's' and 'p') behind the modulator. The relatively high difference 61 between the high intensity level and the low intensity level 62 results in a strong photo acoustic signal.

FIG. 6b shows the total light intensity behind the modulator for less stable situations, e.g. when the detector is subject to large shocks (e.g. when someone is walking with the detector in his hands). The polarization rotator 81 rotates the polarization of the light beam, such that more light with the polarization that is not affected by the modulator ('p' component) is sent to the modulator. The difference 63 between the high intensity level and the low intensity level 64 is now much smaller, but the intensity level 64 of the light that is used for the feedback loop is increased. As a result the photo acoustic signal will be less strong, but the cavity locking feedback loop will perform much better.

Figure 7:
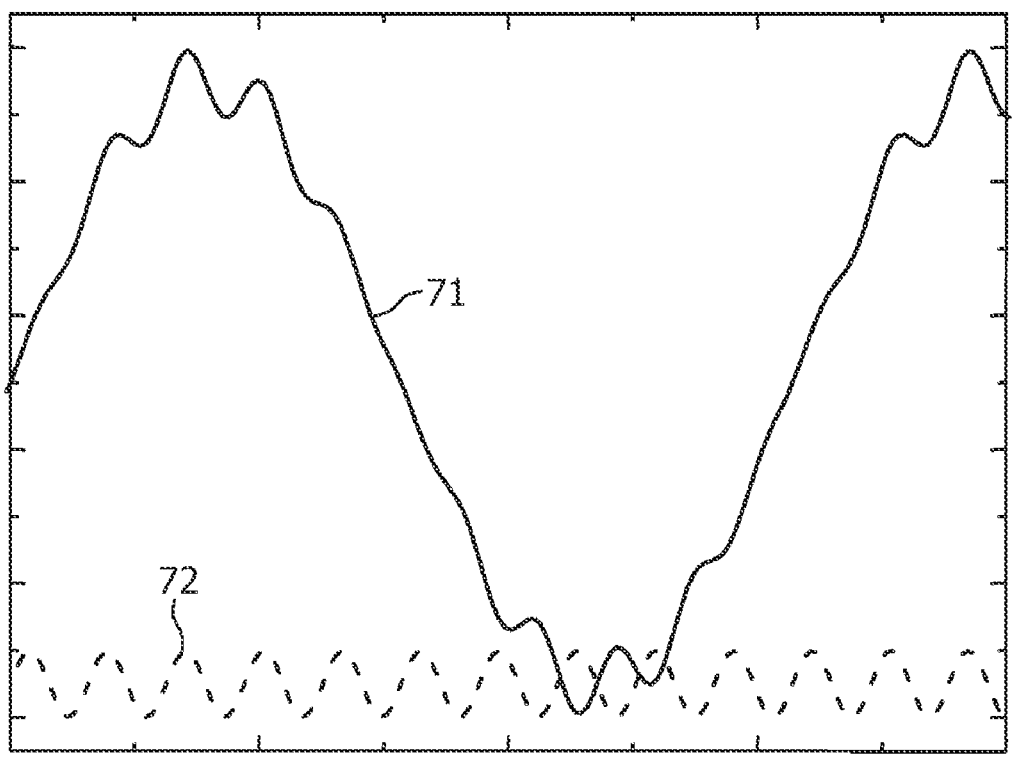
FIG. 7 shows a time dependence of the light intensity for modulated light with two different polarizations according to an embodiment of the invention comprising a polarization dependent modulator.

FIG. 7 shows a time dependence of the light intensity for modulated light for both different polarizations downstream of the cavity according to an embodiment of the invention comprising a polarization dependent modulator. These intensities may be measured separately by placing a polarizing beam splitter 82 behind the optical cavity and providing two separate photo detectors 83, 84 for measuring the intensity of the light with the corresponding polarizations. FIG. 7 shows the light intensities of both polarizations downstream of the cavity. An 's' polarized beam 71 has both a low frequency modulation for photo acoustic signal generation and a high frequency component of the laser wavelength modulation. A 'p' polarized beam 72 only has the high frequency wavelength modulation. Locking the 'p' polarized beam 72 to the cavity can be done very stably because the large difference in intensity, as was present in the embodiment shown in FIG. 5, is absent. The wavelength shifts 54 are no longer present since the feedback beam is separated from the photo-acoustic beam. The amount of feedback signal can be simply adjusted by a further rotation of the laser polarization. It is assumed that the coupling of 's' and 'p' polarized light to the cavity is equal, a fair assumption for an axially symmetric cavity.

It is to be noted that the advantageous combination of an optical cavity and a crystal oscillator could, in principal, also be achieved in trace gas detectors using different feedback loops and/or modulation schemes. When crystal oscillators are used instead of microphones it is important to use a chopping frequency that matches a resonance frequency of the crystal oscillator.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the claims enumerating several means, several of these means may be embodied by one and the same item of hardware. The mere fact that certain measures are recited in mutually different dependent claims does not indicate that a combination of these measures cannot be used to advantage.

What is claim is:

1. A photo acoustic trace gas detector for detecting a concentration of a trace gas in a gas mixture, the photo acoustic trace gas detector comprising:
    a light source for producing a light beam;
    a light modulator for modulating the light beam into a first light that is continuous and has an intensity that varies between a non-zero lower light intensity level and a higher light intensity level for generating sound waves in the gas mixture, an amplitude of the sound waves being a measure of the concentration;
    an optical cavity for containing the gas mixture and for amplifying the continuous light;
    a transducer for converting the sound waves into electrical signals; and
    a feedback loop for regulating the amplification of the continuous light in the optical cavity, the feedback loop comprising a photo detector for measuring the continuous light that passes through the optical cavity,
    wherein the light modulator is arranged for modulating light with a first polarization while not modulating light with a second polarization; and
    wherein the feedback loop comprises means for only providing the light with the second polarization to the photo detector.

2. The photo acoustic trace gas detector as claimed in claim 1, further comprising a unit for adjusting an amplitude of the lower intensity level.

3. The photo acoustic trace gas detector as claimed in claim 1, further comprising a polarization rotator, placed between the light source and the light modulator, for enabling varying a ratio of an intensity of the light with the first polarization and an intensity of the light with the second polarization.

4. The photo acoustic trace gas detector as claimed in claim 1, wherein the light modulator comprises a rotatable disc with at least a first portion with a first non-zero transmission coefficient and a second portion with a second transmission coefficient, the second transmission coefficient being higher than the first transmission coefficient.

5. The photo acoustic trace gas detector as claimed in claim 1, wherein the transducer is a crystal oscillator.

6. The photo acoustic trace gas detector as claimed in claim 5, wherein the crystal oscillator is a quartz tuning fork.

7. A photo acoustic trace gas detector for detecting a concentration of a trace gas in a gas mixture, the photo acoustic trace gas detector comprising:
    a light source for producing a light beam;
    a light modulator for modulating the light beam into a series of light pulses for generating sound waves in the gas mixture, an amplitude of the sound waves being a measure of the concentration,
    an optical cavity for containing the gas, mixture and for amplification of a light intensity of the light pulses,
    a transducer for converting the sound waves into electrical signals, and
    a feedback loop for regulating the amplification of the light intensity of the light pulses in the optical cavity, the feedback loop comprising a photo detector for measuring the light intensity of the light pulses,
    wherein the light modulator is arranged for modulating the light beam between a non-zero lower intensity level and a higher intensity level;
    wherein the light modulator is arranged for modulating light with a first polarization while not modulating light with a second polarization; and
    wherein the feedback loop comprises means for only providing the light with the second polarization to the photo detector.

8. The photo acoustic trace gas detector as claimed in claim 7, further comprising a polarization rotator, placed between the light source and the light modulator, for enabling varying a ratio of an intensity of the light with the first polarization and an intensity of the light with the second polarization.

* * * * *